United States Patent [19]
Gahnberg et al.

[11] Patent Number: 5,172,691
[45] Date of Patent: Dec. 22, 1992

[54] LIMITLESS ROTARY PACING CURRENT CONTROL METHOD AND APPARATUS

[75] Inventors: Loren W. Gahnberg, Mill Creek; Charles A. Couche; Peter Y. Choi, both of Seattle; Christopher Pearce, Monroe, all of Wash.

[73] Assignee: Physio-Control Corporation, Redmond, Wash.

[21] Appl. No.: 640,056

[22] Filed: Jan. 11, 1991

[51] Int. Cl.⁵ ............................................. A61N 1/362
[52] U.S. Cl. ............................................. 128/419 PG
[58] Field of Search .................. 128/419 PG, 419 PT

[56] References Cited

U.S. PATENT DOCUMENTS

| | | | |
|---|---|---|---|
| 3,945,387 | 3/1976 | Adams | 128/419 PG |
| 4,016,432 | 4/1977 | Marzalek | 307/514 |
| 4,073,011 | 2/1978 | Cherry et al. | 128/702 |
| 4,379,245 | 4/1983 | Goldstein | 310/339 |
| 4,436,093 | 3/1984 | Belt | 128/419 PG |

Primary Examiner—William E. Kamm
Attorney, Agent, or Firm—Christensen, O'Connor, Johnson & Kindness

[57] ABSTRACT

A pacemaker/monitor (10) is disclosed for applying a pacing current to a patient through a pair of pacing electrodes (12). The pacemaker/monitor includes a plurality of manual inputs (26) for use by an operator and a microprocessor (16) that responds to programmed instructions stored in read-only memory (20). Cooperatively, these components control the operation of the pacemaker/monitor. In that regard, the desired magnitude of the pacing current in input to the pacemaker/monitor via a limitless rotary current control (46), formed by a rotary pulse generator (52) and a decoder circuit (50). The microprocessor monitors the operation of the various manual inputs and sets the pacing current to zero milliamperes in the event one of the inputs is used, regardless of the position of the rotary pulse generator. For example, when the pacemaker/monitor is turned ON, or the pacing mode of operation is selected, the pacing current is zeroed. Subsequent adjustments in the pacing current are then governed by the microprocessor in response to rotation of the rotary pulse generator. The use of the rotary pulse generator advantageously allows the pacing current level to be quickly adjusted, while the automatic rezeroing of the pacing current decreases the likelihood of an unduly high and potentially painful pacing current being inadvertently applied to the patient.

15 Claims, 4 Drawing Sheets

LIMITLESS ROTARY PACING CURRENT CONTROL METHOD AND APPARATUS

FIELD OF THE INVENTION

This invention relates generally to pacemakers and, more particularly, to controls for such pacemakers.

BACKGROUND OF THE INVENTION

Pacemakers have long been used to stimulate the proper operation of patients' hearts. In a healthy heart, the sinoatrial node produces periodic electrical pulses that travel downward across the atria and ventricles. The spread of each pulse depolarizes the muscle fibers and, after the pulse passes, the fibers contract, repolarize, and return to their resting state. The operation of the heart in this manner pumps blood throughout the cardiovascular system.

The ability of the sinoatrial node to successfully fulfill its obligations as the heart's natural pacemaker can, however, be impaired by coronary disease and injury. In such instances, it may be necessary to apply artificially generated electrical pulses to the heart to stimulate proper operation. These pulses are generally produced by an implantable or external pacemaker.

Reviewing, for example, the construction and operation of an external pacemaker in greater detail, a pair of pacing electrodes is applied to the patient's chest. These electrodes may be positioned in an anterior/anterior configuration or an anterior/posterior configuration as desired. The electrodes are connected to the remotely positioned pacemaker by cables.

The pacemaker typically includes a number of controls that allow medical personnel to regulate the operation of the pacemaker. In that regard, if the pacemaker is part of a more comprehensive system that includes, for example, an electrocardiogram (ECG) monitor and defibrillator, a button or switch for selecting the pacing mode of operation is typically included.

In addition, most external pacemakers include a button or switch that allows the operator to select between two different modes of pacing operation: continuous and demand. In the continuous mode of operation, pacing signals are continuously applied to the patient until pacing is manually disrupted by the operator. In the demand mode of operation, the patient's ECG signals are monitored and the pacemaker determines when pacing is to be performed.

The pacemaker also usually includes controls that allow the operator to regulate the nature of the pacing signals applied to the patient. In that regard, a button or switch may be included to allow the operator to adjust the rate at which electrical pulses are applied to the patient. Further, the pacemaker may include a button or switch that the operator can use to adjust the magnitude of the pacing current applied to the patient. In that regard, the magnitude selected will usually be the lowest one that is sufficient to "capture" the heart, or restore it to proper operation. Finally, a START/STOP button is generally included to initiate pacing after the various other inputs have been provided.

One example of a conventional pacing system is provided by the LIFEPAK 10 external pacemaker/monitor/defibrillator, available from Physio-Control Corporation, the assignee of the present application. Among the various controls associated with this product is a "PACEMAKER" pushbutton that enables the pacing portion of the instrument.

A toggled, "RATE" pushbutton allows the rate at which electrical pulses are produced to be input by the operator. More particularly, the operator can increment the pacing rate by depressing one side of the pushbutton and can decrement the pacing rate by depressing the other side of the pushbutton. The product is microprocessor based and responds to actuations of the RATE pushbutton in accordance with software instructions programmed into memory to achieve the desired rate regulation.

The LIFEPAK 10 product also includes four pushbuttons that allow the operator to adjust the magnitude of the pacing current. For example, the operator can increase or decrease the pacing current in five-milliampere increments by depressing separate "5" milliampere pushbuttons. Similarly, separate "20" milliampere pushbuttons are provided to allow the pacing current to be increased and decreased in 20-milliampere increments.

As with the rate control pushbutton, the instrument's microprocessor responds to actuations of the four current control pushbuttons in accordance with software instructions programmed into the instrument. In addition, the software instructs the microprocessor to monitor the operation of, for example, the PACEMAKER and START/STOP buttons to automatically reset the pacing current to zero in the event either switch is actuated. As a result, at startup, the pacing current defaults to zero, regardless of the last setting established with the four pacing current pushbuttons.

The inclusion of this reset feature ensures that the initial application of a nonzero pacing current to a patient is the result of a specific operation action. Such a limitation is important, in part, because the unintentional application of an unduly high pacing current level may needlessly increase pain or discomfort experienced by the patient as a result of the pacing operation.

As an alternative to the use of pushbutton switches of the type described above, potentiometers have also been used to allow an operator to regulate the magnitude of the pacing current applied. One example of a defibrillator/monitor/pacemaker that employs a potentiometer for pacing current control is the LIFEPAK 8 product sold by Physio-Control Corporation, the assignee of the present application. The use of such a rotary device has the advantage of allowing an operator to adjust the pacing current level more quickly than can conventionally be achieved with pushbutton switches.

The conventional potentiometer used in the LIFEPAK 8 product, however, has a limited range of rotation, with each rotational position having a particular resistance and, hence, pacing current associated therewith. As a result, the LIFEPAK 8 defibrillator/monitor/pacemaker produces a zero pacing current upon startup only if the potentiometer is manually rotated to its zero position before pacing is initiated. In emergency situations, this manual step can easily be forgotten.

The LIFEPAK 8 and LIFEPAK 10 products discussed above both employ a mechanism for selecting the pacing operation, as well as a pacing START/STOP button. As suggested above, the inclusion of a separate START/STOP pushbutton requires the operator to actively initiate pacing. Thus, pacing is unlikely to begin at an inadvertently set rate or current level. The inclusion of the START/STOP pushbutton on the defibrillator/monitor/pacemaker does, however, contribute to the complexity of the instrument's control panel.

In view of these observations, it would be desirable to produce a pacemaker control system that allows an operator to quickly and precisely control the magnitude of the pacing current applied. The control system should also ensure that the pacing current is automatically reset to zero at the initiation of pacing. Finally, the inputs to the pacemaker control system should preferably be limited to the minimum required for proper operation.

SUMMARY OF THE INVENTION

In accordance with this invention, a pacemaker, responsive to at least one manual input, is disclosed for producing a controllable pacing current. The pacemaker includes a current controller for rotationally producing an input indicative of the pacing current to be produced and for resetting that output to be indicative of a zero pacing current in response to the manual input. The controllable current source, responsive to the output of the current controller, is also included for producing the pacing current.

In one arrangement, the current controller includes an input device and a processor. The input device is for rotationally producing an output indicative of the pacing current to be produced. The processor is for monitoring the actuation of the pacemaker and for resetting the output of the input device to be indicative of a zero pacing current in response to the manual input.

The input device may include a rotatable knob, a shaft coupled to the knob, and a codewheel, coupled to the shaft. A light emitter is employed to transmit light to the codewheel, with the codewheel modulating the light when rotated. A light detector detects the modulation of light by the codewheel to produce an electrical response. Finally, a converter converts the electrical response into the output indicative of the pacing current to be produced.

A method of controlling the pacing current to be delivered by a pacemaker is also disclosed. The method includes the steps of responding to a manual input provided on the pacemaker. The rotation of a rotary pacing current control knob is also monitored. The pacing current is established at zero for the initial rotational position of the control knob in response to operation of the manual input. The pacing current is then adjusted as rotation of the control knob from the initial rotational position is monitored.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT

Figure 1:
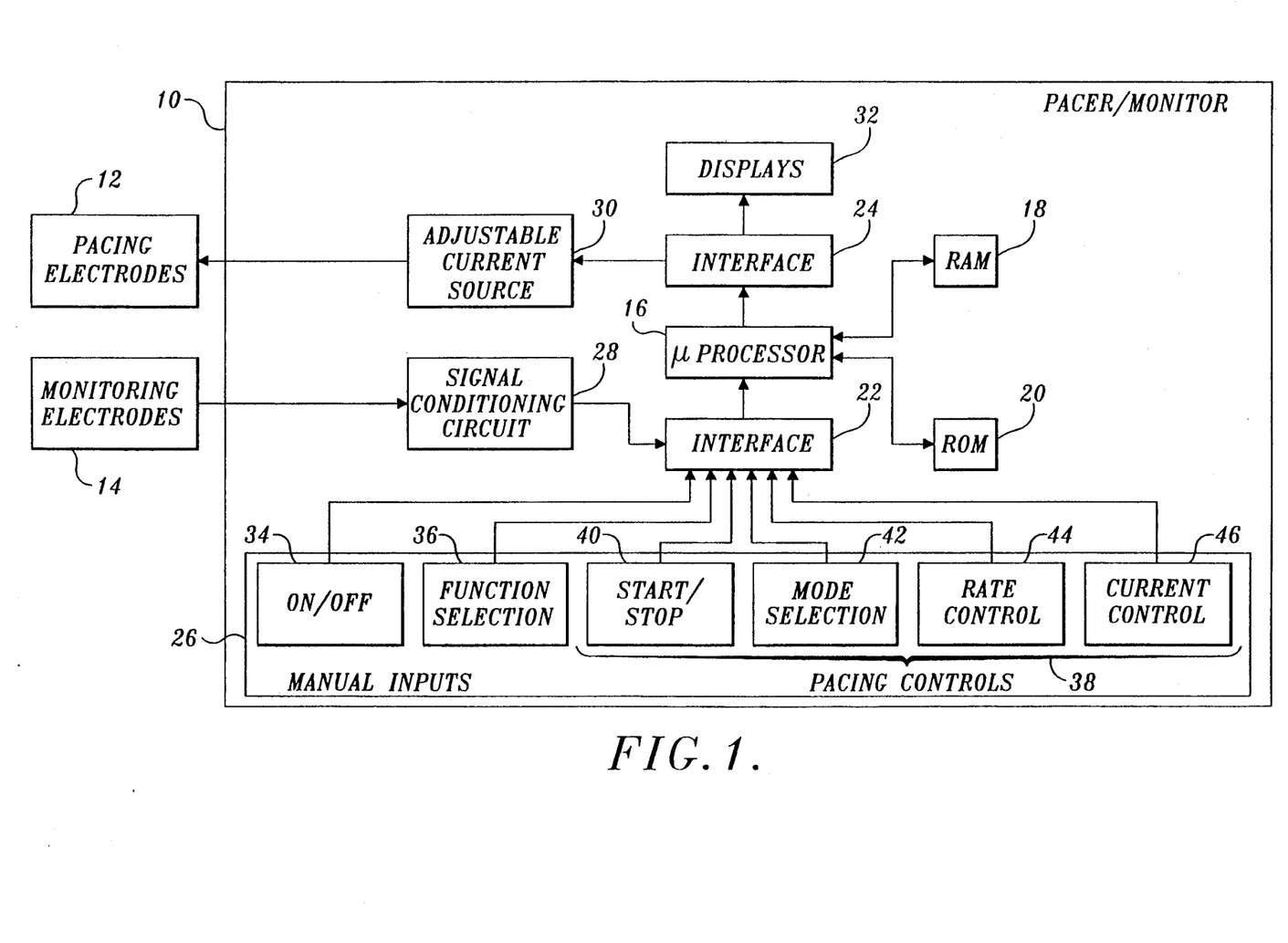
FIG. 1 is a block diagram of a pacemaker/monitor including a pacing current control system constructed in accordance with the invention.

Referring now to FIG. 1, a pacemaker/monitor 10, constructed in accordance with this invention, is shown. As will be described in greater detail, the pacemaker/monitor 10 is constructed to allow an operator to rapidly adjust the magnitude of the pacing current applied by pacemaker/monitor 10 to a patient. The pacemaker/monitor 10 is also constructed, however, to reset the pacing current level to zero under certain circumstances, independent of prior inputs by the operator. As a result, the unintentional application of unduly high pacing current levels to a patient is avoided.

As shown in FIG. 1, the pacemaker/monitor 10 is coupled to a pair of pacing electrodes 12 and a plurality of monitoring electrodes 14. The pacing electrodes 12 are attached to a patient (not shown) and allow the pacemaker/monitor 10 to apply pacing current pulses to the patient. The monitoring electrodes 14 are also attached to the patient and allow the pacemaker/monitor 10 to receive the patient's ECG signals.

Addressing these components in greater detail, the pacing electrodes 12 and monitoring electrodes 14 are of conventional design. In that regard, pacing electrodes 12 are typically adhesively applied to the patient's chest and are constructed to provide a low-impedance interface between the patient and the pacemaker/monitor 10. The monitoring electrodes 14 are likewise preferably adhesively attached to the patient and constructed to provide a low-impedance interface between the patient and the pacemaker/monitor 10. Typically, three monitoring electrodes 14 are employed.

With regard to the pacemaker/monitor 10, for the purposes of the ensuing discussion, the primary function of the pacemaker/monitor 10 is the performance of pacing. The pacemaker/monitor 10 illustrated in FIG. 1 is, however, designed to also monitor the patient's ECG activity. As will be appreciated, the pacemaker/monitor 10 may further be constructed to perform a variety of other functions including, for example, defibrillation and synchronized cardioversion.

Addressing now the construction of pacemaker/monitor 10 in greater detail, as shown in FIG. 1, the pacemaker/monitor 10 includes a number of components. The basic core of the pacemaker/monitor 10 is formed by a microprocessor 16, random-access memory (RAM) 18, read-only memory (ROM) 20, and input and output interfaces 22 and 24, respectively. As will be described in greater detail below, the microprocessor 16 receives input information from a variety of sources via interface 22. In accordance with software instructions stored in ROM 20, the microprocessor 16 processes these various inputs, retaining information in RAM 18 as needed, to provide the various outputs of the pacemaker/monitor 10 at interface 24.

These core components are of conventional design and their construction, interrelationship, and operation are well known in the art. As a result, the discussion of these components is limited. Additional details concerning the construction and use of these core components can be obtained from any of myriad texts reviewing basic microprocessor-based system design.

Reviewing now the noncore components of pacemaker/monitor 10, as shown in FIG. 1, the microprocessor 16 receives a number of inputs, via input interface 22, from a manual inputs block 26 and from a signal-conditioning circuit 28. Similarly, the microprocessor 16 provides outputs via output interface 24 to an adjustable current source 30 and displays 32.

Reviewing each of these components individually, the manual inputs block 26 allows an operator to manually provide the microprocessor 16 with information concerning the desired operation of the pacemaker/monitor 10. The construction and operation of the various components included in block 26 will be discussed in greater detail below.

The signal-conditioning circuit 28 receives the ECG signals from the monitoring electrodes 14 and processes them for analysis by the microprocessor 16. As will be appreciated, the signal-conditioning circuit 28 is of conventional design and typically includes, among other elements, a preamplifier. The preamplifier amplifies ECG signals sensed at the monitoring electrodes 14 to levels suitable for receipt and analysis by microprocessor 16. An analog-to-digital (A/D) converter, also included as part of signal-conditioning circuit 28, converts the analog ECG signals into a digital form usable by the microprocessor 16.

The signal-conditioning circuit 28 further typically includes an isolation circuit for electrically isolating the monitoring electrodes 14 from the remainder of the pacemaker/monitor 10. Isolation may be achieved, for example, by optically, rather than electrically, transmitting signals sensed at the monitoring electrodes 14 to the remainder of pacemaker/monitor 10. The isolation circuit protects the patient from potential injury in the event of an electrical fault at the pacemaker/monitor 10 and, likewise, protects the pacemaker/monitor 10 from potentially damaging signals applied to the monitoring electrodes 14.

The adjustable current source 30 is also of conventional design. Current source 30 is constructed to produce pacing signals that include, for example, a series of monophasic, truncated exponential pulses having 20-millisecond durations and variable refractory periods. The current source 30 is also designed to allow the repetition rate, as well as amplitude of the pulses, to be controlled.

As will be appreciated, the current source 30 may include a digital-to-analog (D/A) converter for converting digital outputs from microprocessor 16 into an analog format used by the remainder of the components to control variable parameters of the pacing signal. The current source 30 also typically includes, for example, a waveform-conditioning circuit that produces the desired pulse waveform and a controllable-gain amplifier that governs the magnitude of the pacing current applied to the pacing electrodes 12.

Regarding the displays 32 provided by the pacemaker/monitor 10, as will be appreciated, both visible and audible displays 32 may be employed. For example, ECG waveforms developed by microprocessor 16 in response to signals sensed from various monitoring electrodes 14 may be graphically displayed. In addition, the magnitude and rate of the pacing pulses applied to the patient by the pacing electrodes 12 may be numerically displayed. Typically, such visible displays 30 are provided on a front panel of the pacemaker/monitor 10.

Having briefly reviewed the various components of the pacemaker/monitor 10, the manual inputs 26 will now be discussed in greater detail. Although numerous other manual inputs 26 may be employed, the manual inputs 26 shown in FIG. 1 are representative of those commonly included in a device such as pacemaker/monitor 10. The manual inputs 26 shown include an ON/OFF control 34, a function selection control 36, and four pacing controls 38. The pacing controls 38, in turn, include a START/STOP control 40, mode selection control 42, rate control 44, and current control 46.

Reviewing each of the manual inputs 26 individually, the ON/OFF control 34 is the main power control for the pacemaker/monitor 10. The ON/OFF control 34, thus, allows the operator to turn the pacemaker/monitor 10 ON and OFF as desired. As will be appreciated, the ON/OFF control 34 may be, for example, a pushbutton or a switch.

The function selection control 36 is included on a multiple-function device, such as pacemaker/monitor 10, to allow the device to be selectively switched between various modes of operation. For example, the pacemaker/monitor 10 may be selectively switched between pacing and monitoring modes of operation. As will be discussed in greater detail below, if defibrillation capabilities are added to the pacemaker/monitor 10, the function selection control 36 would also allow a defibrillation mode of operation to be selected. The function selection control 32 may, for example, be a multiple-position switch whose positions correspond to the different modes of operation to be selected, a single pushbutton for use in selecting the desired mode of operation from a menu of modes scrolled by the microprocessor 16, or a plurality of separate pushbuttons associated with the different modes of operation.

The remaining manual inputs 26 are the pacing controls 38, which are responsible for regulating various aspects of pacemaker/monitor 10 operation in the pacing mode. The first of the pacing controls 38 to be discussed is the START/STOP control 40. The START/STOP control 40 is included on many conventional pacemaker/monitors and is typically a single pushbutton used to initiate the application of pacing signals to the patient once the various other pacing controls 38 have been appropriately actuated.

As will be appreciated, the inclusion of START/STOP control 40 on pacemaker/monitor 10 ensures that the initial application of pacing pulses to the patient is the result of a positive action on the part of the operator. Thus, the likelihood that pacing signals having previously established parameters will be inadvertently applied to the patient is reduced. Because the pacing current level previously selected to capture an unconscious patient may be unsuitable for, and painful to, a conscious patient, this feature has traditionally been important for product acceptance.

One aspect of the present invention, however, is the optional omission of the conventional START/STOP control 40 from the pacemaker/monitor 10. In that regard, as described in greater detail below, the pacemaker/monitor 10 automatically resets the pacing current level to zero milliamperes when, for example, the pacemaker/monitor 10 is turned ON or a new mode of operation, such as defibrillation, is selected. As a result, whenever the pacing mode of operation is selected of first performed, the magnitude of the pacing current will be zero milliamperes until the operator actively adjusts the pacing current to a different, nonzero level. With such an automatic current-resetting feature, the inclusion of a conventional START/STOP control 40 on the pacemaker/monitor 10 is of limited value and can be omitted, while still ensuring that previously established and potentially undesirable pacing currents are not unintentionally applied to the patient.

By omitting the START/STOP control 40, the complexity of the control panel on the pacemaker/monitor 10 can advantageously be reduced.

The next one of the pacing controls 38 to be discussed is the mode selection control 42. With the function selection control 36 used to select the pacing mode of operation for pacemaker/monitor 10, the mode selection control 42 then allows the operator to select between two alternative submodes of pacing operation. In that regard, the mode selection control 42 may be, for example, a two-position switch or a pair of pushbuttons that can be selectively actuated to cause the pacemaker/monitor 10 to operate in either a "demand" or "nondemand" pacing submode.

Reviewing these two submodes of operation, the pacemaker/monitor 10 normally operates in the demand submode. In this submode, the microprocessor 16 analyzes the ECG signals received from monitoring electrodes 14 in accordance with software instructions stored in ROM 20 and initiates the application of pacing pulses to the pacing electrodes 12 in response to certain predetermined characteristics of the ECG signals. Thus, pacing in the demand submode of operation is typically performed only periodically and in response to the patient's condition.

In the nondemand, or asynchronous, pacing submode, on the other hand, the microprocessor 16 causes the adjustable current source 30 to produce a continuous sequence of pacing pulses in response to inputs from the pacing controls 38. Specifically, the application of pacing pulses to the patient is initiated and discontinued in response to, for example, actuation of the START/STOP control 40. The pacemaker/monitor 10 is only rarely operated in the nondemand submode.

The next one of the pacing controls 38 to be discussed is the rate control 44. As will be appreciated, the rate control 44 allows the operator to set the rate at which pacing pulses are applied to the patient and, hence, the desired heart rate for the patient. The rate control 44 allows the rate to be set over a range extending, for example, between 40 and 170 beats per minute. The rate control 40 may be formed by a rotary potentiometer whose various rotary positions correspond to the alternative heartbeat settings or separate pushbuttons for continuously or incrementally increasing and decreasing the rate.

Finally, and of greatest importance for the present application, the pacing controls 38 also include a current control 46. The current control 46 allows the operator to control the magnitude of the pacing current to be applied to the patient via the pacing electrodes 12. Unlike prior art arrangements, the current control 46 of the present invention is provided, in part, by a limitless rotary control.

Figure 2:
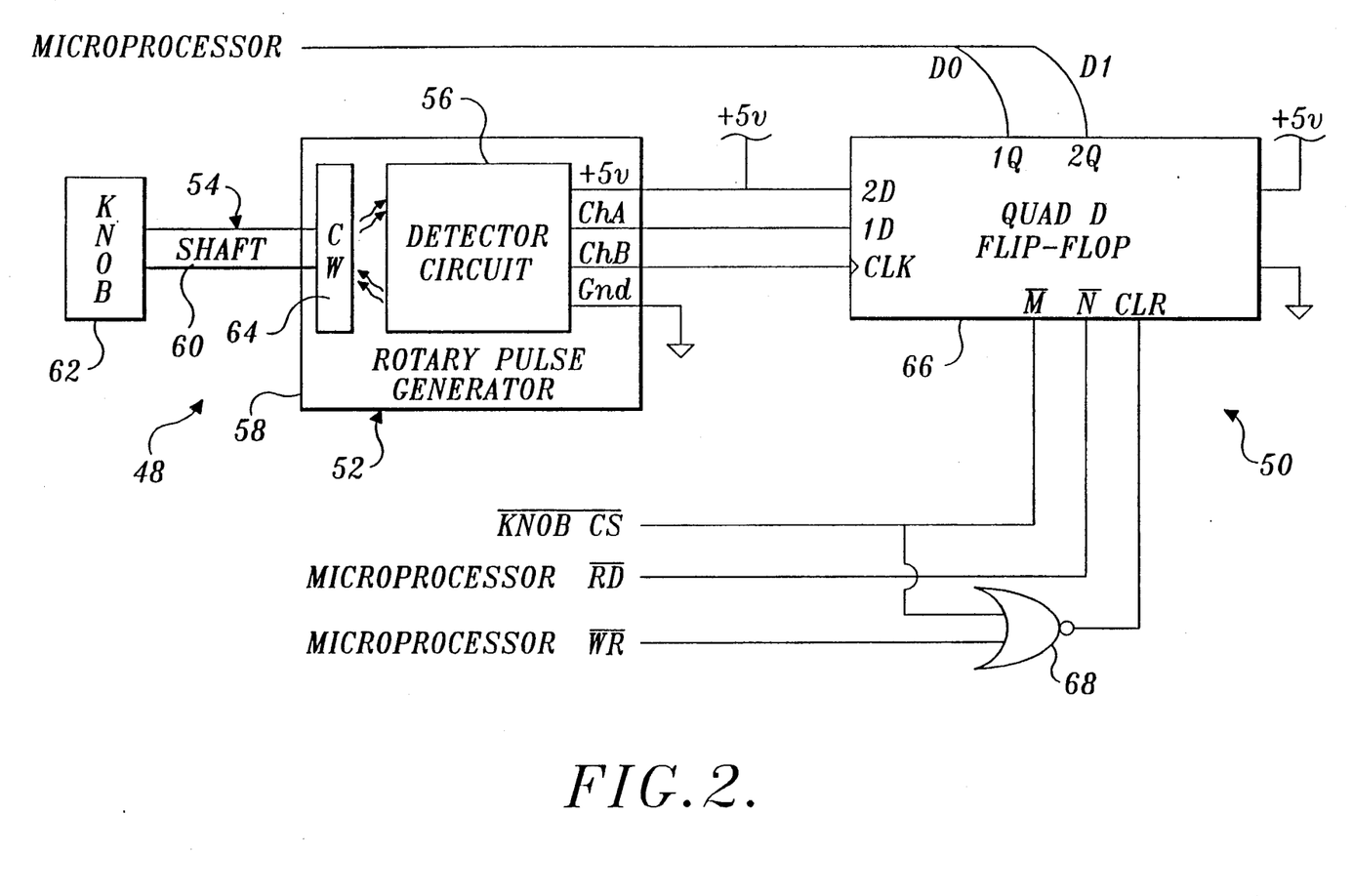
FIG. 2 is a more detailed block diagram of a rotary pulse generator and associated processing circuit included as part of a current control input in FIG. 1.

Discussing the current control 46 in greater detail, reference is had to FIG. 2. Although any of a number of different constructions can be employed, in the arrangement shown, the current control 46 includes an input device 48 and a decoder circuit 50. Briefly, the input device 48 converts a manual action by the operator into a signal indicative of the current level desired. The decoder circuit 50 then converts this signal into a form that is more readily usable by microprocessor 16.

Reviewing these components individually, the input device 48 is preferably a conventional rotary pulse generator (RPG) 52 of the type sold by the Hewlett-Packard Co. under the HRPG series designation. As schematically shown in FIG. 2, the RPG 52 includes a specular codewheel assembly 54 and a detector circuit 56, supported by a common housing 58 that is attached to the front panel of the pacemaker/monitor 10. More particularly, the specular codewheel assembly 54 includes a shaft 60, which is rotatably supported relative to the detector circuit 56 by housing 58, a knob 62 for use by the operator in rotating shaft 60, and a codewheel (CW) 64 for optically cooperating with the detector circuit 56 to produce an output indicative of the rotation of shaft 60. The detector circuit 56 includes a light source (not shown) for illuminating the codewheel 64. A photosensitive circuit (not shown) is included to receive light from the source after it is reflected by the codewheel 64 and to produce at least one output representative of the codewheel's motion.

The RPG 52 operates in the following manner. As noted, the light source in the detector circuit 56 emits a beam of light onto the surface of the codewheel 64. The codewheel 64, in turn, reflects at least some of the light back to the photosensitive circuit. As the operator rotates the knob 63, the codewheel 64 also rotates, modulating the light received at the photosensitive circuit accordingly.

Figure 3A:
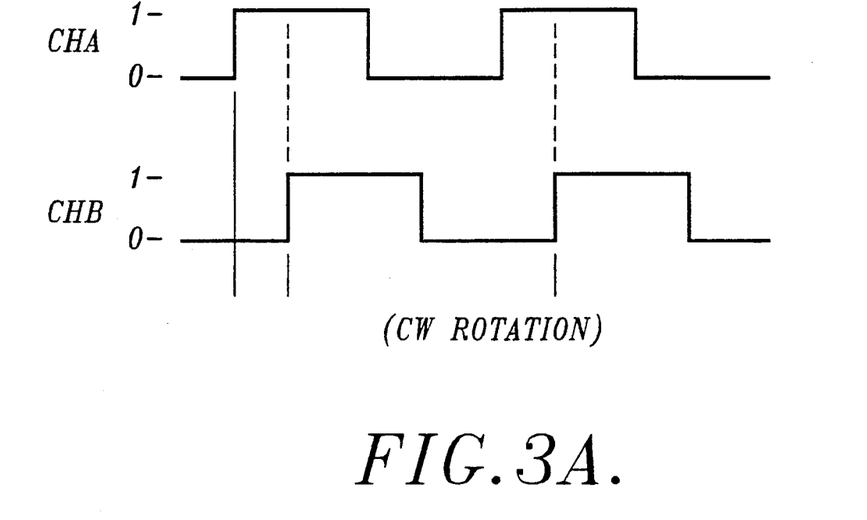
FIGS. 3A and 3B illustrate outputs produced by the rotary pulse generator and associated processing circuit of FIG. 2 in response to rotation of the pulse generator in clockwise and counterclockwise directions.
Figure 3B:
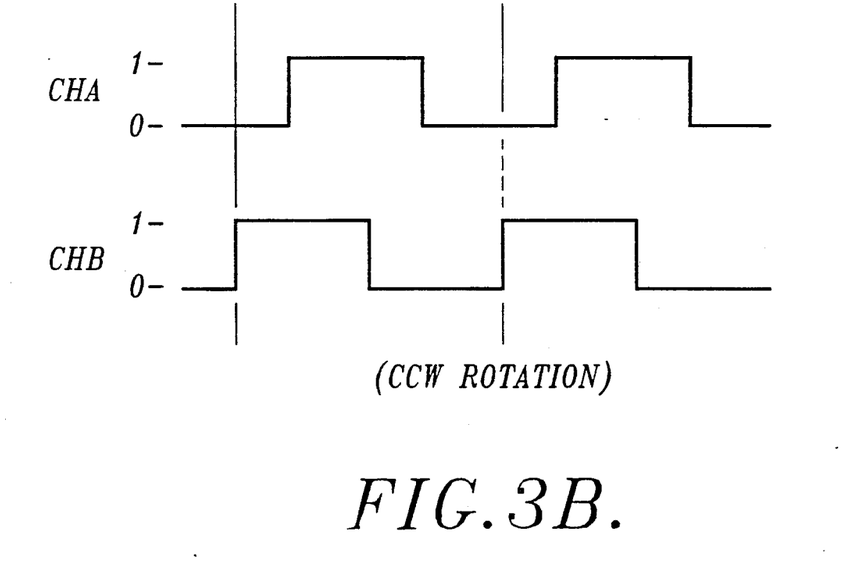

In that regard, the detector circuit includes four terminals, designated +V, channel A, channel B, and ground. As shown in FIG. 2, the +V terminal is an input and is connected to a +V voltage source that powers the various components of the detector circuit 56. The channel A and channel B terminals, on the other hand, are outputs. Each output is a square wave that alternates between high and low levels in response to rotation of the codewheel 64. As shown in FIGS. 3A and 3B, the channel A output leads the channel B output when the codewheel 64 is rotated clockwise, while the channel B output leads the channel A output when codewheel 64 is rotated counterclockwise. The channel A and channel B outputs are not used to determine some absolute position of the RPG 52 but, rather, to determine rotation of the RPG 52 from its initial or rezeroed position.

As will be appreciated, the RPG 52 is a limitless device that can be rotated endlessly in either direction, without restriction. In the present arrangement, however, the available pacing current range is between zero and 200 milliamperes and the maximum possible pacing current adjustment of 200 milliamperes is input by turning the RPG 52 through, for example, two full rotations. Although the RPG 52 can be freely rotated beyond that point, such additional rotation is ignored by microprocessor 16.

To elaborate upon how the outputs of the RPG 52 are used to achieve current control, reference is again had to FIG. 2. As shown, the channel A and channel B outputs of RPG 52 are applied to the decoder circuit 50. The function of the decoder circuit 50 is to receive the two outputs and convert them into a form that microprocessor 16 can more readily use to identify the rotation of the codewheel 64 initiated by the operator and, hence, the desired adjustment in the magnitude of the pacing current.

In the arrangement shown, the decoder circuit 50 includes a D-type flip-flop circuit 66. As will be appreciated, D-type flip-flops allow the state of input data to be determined at precisely defined times and then retained for a period of time thereafter. In the present arrangement, the D-type flip-flop circuit 66 allows the alternations of the channel A and channel B inputs between the high and low levels to be more easily monitored by the microprocessor 16 to determine the rotation of the RPG 52.

Addressing the construction and operation of flip-flop circuit 66 in greater detail, as indicated in FIG. 2, it has a quadruple configuration including four D-type flip-flops in a single integrated circuit although, as described in greater detail below, only two of the flip-flops are used. The circuit 66 includes a plurality of terminals, such as a clock (CLK) input terminal, a clear (CLR) input terminal, a 1D input terminal and 1Q output terminal associated with a first D-type flip-flop, a 2D input terminal and 2Q output terminal associated with a second D-type flip-flop, $\overline{M}$ and $\overline{N}$ input terminals, and power supply terminals.

Reviewing the connections of these various terminals, as shown in FIG. 2, three inputs applied to the $\overline{M}$, $\overline{N}$, and CLR terminals cooperatively allow data from RPG 52 to be accessed or read. More particularly, the complement of a knob chip select output ($\overline{KNOB\ CS}$) is applied to input terminal $\overline{M}$. The output $\overline{KNOB\ CS}$ is produced by an input/output device selection chip (not shown in FIG. 2) when microprocessor 16 wants to communicate with RPG 52, as opposed to other input/output devices. Similarly, the complement of a read data output ($\overline{RD}$) from microprocessor 16 is applied to input terminal $\overline{N}$ and the NOR combination of the KNOB CS output and the complement of a write data output ($\overline{WR}$) from microprocessor 16, produced at a NOR gate 68, is applied to the CLR input.

In addition, the flip-flop circuit 66 includes several data inputs and outputs. For example, the channel A and channel B outputs of RPG 52 are connected to the 1D and CLK input terminals of flip-flop circuit 66. The +V power supply is connected to the 2D input terminal. The flip-flop circuit 66 responds to these inputs by producing two outputs D0 and D1 at terminals 1Q and 2Q for use by microprocessor 16 in evaluating the rotation of RPG 52.

Having briefly reviewed the connections to the flip-flop circuit 66, the manner in which circuit 66 responds to the operation of microprocessor 16 and RPG 52 will now be discussed. When the microprocessor 16 wants to read data from the RPG 52, it causes the $\overline{KNOB\ CS}$ and $\overline{RD}$ inputs to flip-flop circuit 66 to drop to a low logic level. As a result, the D0 and D1 outputs produced by flip-flop circuit 66 in response to the channel A and channel B inputs are placed on the databus for transfer to microprocessor 16. After a brief interval, the $\overline{KNOB\ CS}$ and $\overline{RD}$ inputs return to a high logic level and the outputs D0 and D1 revert to a high-impedance, "idle" state.

To clear the flip-flop circuit 66, the microprocessor 16 causes the $\overline{KNOB\ CS}$ and $\overline{WR}$ inputs to drop to a low logic level. These inputs are combined at NOR gate 68, whose output is received at the CLR input to circuit 66. As a result, both flip-flops and the two outputs D0 and D1 are cleared.

Discussing now the way in which the flip-flop circuit 66 responds to the channel A and channel B inputs, as will be appreciated, channel B "clock" pulses are produced only in response to rotation of RPG 52. On the rising edge of each channel B pulse, the output D1 will be set to the same state as the +V input applied to terminal 2D, immediately prior to the channel B pulse. As a result, if accessed by microprocessor 16, the output D1 will be high, like the +V input, when the RPG 52 is rotated.

Similarly, on the rising edge of each channel B clock pulse, the output D0 will be set to the same state as the channel A input, applied to terminal 1D, immediately prior to the channel B pulse. As will be appreciated from the relative phase of the channel A and channel B inputs shown in FIG. 3, the channel A input is high at this point when the RPG 52 is rotated clockwise and low when RPG 52 is rotated counterclockwise. Thus, the output D0 will be high for clockwise rotation of RPG 52.

The D0 and D1 outputs of flip-flop circuit 66 are used by microprocessor 16 to control the pacing current in the following manner. In that regard, the D0 and D1 outputs indicate only whether or not the RPG 52 has been rotated and, if so, the direction of rotation. To determine the pacing current level adjustment required, the microprocessor 16 reads and clears the flip-flop circuit 66, in the manner described above, 540 times per second. Each time the outputs D0 and D1 are read to detect the occurrence and direction of RPG rotation, microprocessor 16 will initiate a predetermined increase (e.g., one milliampere) in the pacing current level if a clockwise rotation of RPG 52 is sensed. On the other hand, if a counterclockwise rotation of RPG 52 is sensed, a corresponding predetermined decrease in the pacing current level is initiated. If the microprocessor 16 determines that RPG 52 has not been rotated, no adjustment is made to the pacing current. The total adjustment in the pacing current level caused by rotation of the RPG 52 a given angular distance is then equal to the cumulative effect of the incremental adjustments made every 1/540 second interval during which rotation is sensed.

Figure 4:
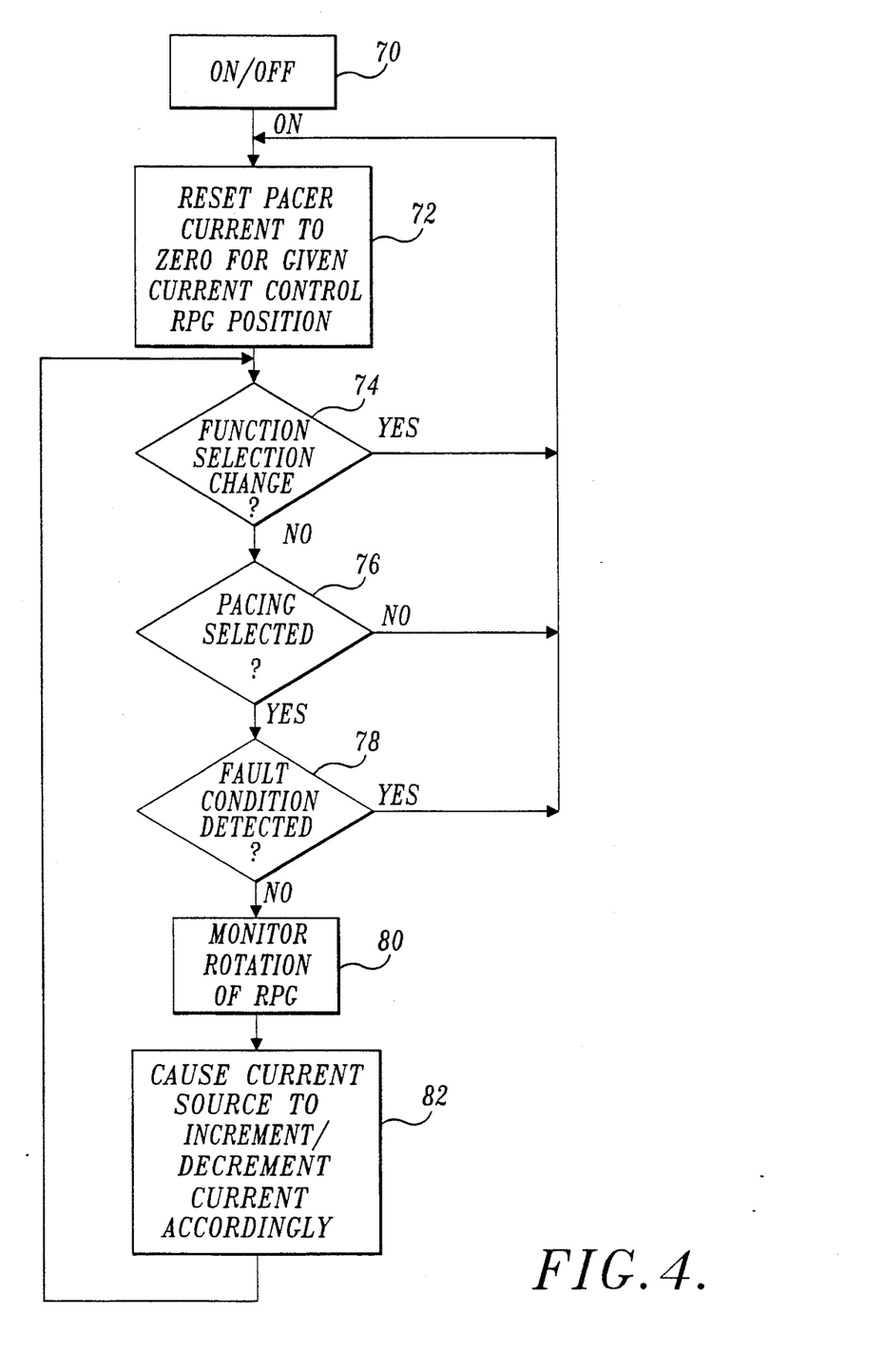
FIG. 4 is a flowchart illustrating the basic operation of the pacing current control system included in the pacemaker/monitor of FIG. 1.

Turning now to a discussion of the manner in which the pacemaker/monitor 10 resets the magnitude of the pacing current to zero milliamperes, reference is made to the flowchart of FIG. 4, which illustrates the operation of microprocessor 16 in response to program instructions stored in ROM 20. In that regard, as indicated at the initial block 70 of the flowchart, the operation of microprocessor 16 begins in response to actuation of the ON/OFF control 34. More particularly, when control 34 is initially actuated to turn the pacemaker/monitor 10 ON, the microprocessor 16 sets the pacing current to zero milliamperes, regardless of the position of the RPG 52 of current control 46. This step is illustrated in block 72 of the flowchart and ensures that the pacing current is always set to zero milliamperes at startup.

At block 74, the microprocessor 16 next determines whether the function selection control 36 has been operated. As will be recalled, the function selection control 36 is used by the operator to switch the pacemaker/monitor 10 between, for example, pacing and monitoring modes of operation. If control 36 has been actuated, microprocessor 16 sets the pacing current level to zero milliamperes at block 72, as described above. In the event that the function selection control 32 has not been used, however, the microprocessor 16 proceeds to perform the operation illustrated by block 76 of the flowchart.

In that regard, at block 76, microprocessor 16 determines whether the START/STOP control 40, if included among the pacing controls 38, has been actuated to initiate or discontinue the pacing operation. If microprocessor 16 determines, at block 76, that pacing is being initiated, the current level has already been set to zero at block 72, via block 74, and the operation of the microprocessor 16 proceeds to block 76. On the other hand, if microprocessor 16 determines that pacing is being discontinued, the microprocessor 16 returns to block 72 and sets the pacing current to zero milliamperes.

Next, at block 78, the microprocessor 16 determines whether a fault condition, such as the improper attachment of the pacing or monitoring electrodes 12 or 14 to the patient, exists. Such a fault condition can be detected, for example, by monitoring the impedance between the electrodes. In the event a fault condition is detected, the pacing current is set to zero milliamperes at block 72, as described above. Otherwise, the microprocessor 16 proceeds to perform the operation illustrated at block 80.

Once the microprocessor 16 has set the pacing current to zero, as represented by block 72, or in the event that microprocessor 16 has determined that the manual inputs 26 have not been changed at blocks 70, 74, and 76, the microprocessor 16 proceeds to perform the operation represented at block 80 of the flowchart. At block 80, the rotation of the current control RPG 52 is monitored. As previously described, the rotation of the RPG 52 is indicative of the change in the magnitude of the pacing current desired by the operator.

Next, at block 82, the microprocessor 16 provides an output to the adjustable current source 30 to increment or decrement the pacing current according to the rotation of the RPG 52 monitored. As noted above, however, the microprocessor 16 limits the maximum pacing current level to 200 milliamperes. Finally, from block 82, the operation of the microprocessor 16 is returned to block 74 and the various ones of the manual inputs 26 are again monitored in sequence.

As will be appreciated, the testing performed at blocks 70, 74, and 76 can be omitted for any one or more of the corresponding manual inputs 24. In that regard, as previously noted, the START/STOP control 40 is not required in the preferred arrangement and step 76 of FIG. 4 is preferably omitted.

On the other hand, it will be appreciated that additional tests can be performed to evaluate the use of other manual inputs 26 not illustrated in FIG. 1. For example, although not shown in FIG. 4, the microprocessor 16 may also determine whether the mode selection control 42 has been actuated at a point, for example, between blocks 74 and 76. In such an arrangement, the pacemaker/monitor 10 has been switched between the normal and demand submodes of operation, as indicated by actuation of control 42, and microprocessor 16 would set the pacing current to zero milliamperes at block 72.

Further, if the pacemaker/monitor 10 is constructed to also allow defibrillation to be performed, the microprocessor 16 can be programmed to monitor the actuation of the various manual inputs associated with that mode of operation. The microprocessor 16 can also be programmed to rezero the pacing current in response to other factors including, for example, the expiration of a set interval of time during which a pacing current is not produced and none of the manual inputs 26 are operated.

It is further noted that the process illustrated by the flowchart of FIG. 4 is just one example of the way in which the various steps required to reset the pacing current to zero can be performed. In that regard, the steps can easily be combined or performed in alternative sequences not illustrated in FIG. 4 directly.

As previously discussed, a pacemaker/monitor 10 constructed in accordance with this invention has numerous advantages. In that regard, the inclusion of a rotary pulse generator 52 allows the pacing current level to be manually adjusted rapidly and effectively. Further, because the pacing current is automatically reset to zero when, for example, the unit is switched on or the pacing mode of operation is selected, an undesirably high pacing current will not be inadvertently applied to the patient. As a result, the application of an uncomfortably high pacing current to the patient may, in certain instances, be avoided. Finally, with this automatic reset feature, the use of a separate START/STOP control is not required because the pacing current is always initially set to zero milliamperes.

Those skilled in the art will recognize that the embodiments of the invention disclosed herein are exemplary in nature and that various changes can be made therein without departing from the scope and the spirit of the invention. In this regard, and as was previously mentioned, the invention is readily embodied with a variety of input controls and software schemes. Further, it will be recognized that other continuous rotary devices can be employed for the current control switch and various other processing circuits can be used in place of the flip-flop circuit and microprocessor. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A method of controlling the pacing current to be delivered by a pacemaker in response to the operation of a manual input element included on the pacemaker and the rotation of a limitless rotary pacing current control included on the pacemaker, said method comprising the steps of:

monitoring the operation of the manual input element included on the pacemaker;

monitoring the rotation of a limitless rotary pacing current control included on the pacemaker;

establishing the pacing current as zero for an initial rotational position of the rotary pacing current control when a predetermined operation of the manual input is monitored; and adjusting the pacing current to an adjusted level in response to rotation of the rotary pacing current control from the initial rotational position.

2. The method of claim 1, wherein the step of monitoring the rotation of the rotary pacing current control comprises the steps of monitoring the magnitude and the direction of rotation and wherein the adjusted level of the pacing current is dependent upon the magnitude and direction of rotation monitored.

3. The method of claim 1, wherein the steps of monitoring the rotation of the rotary pacing current control comprises the steps of:

producing a beam of light;

optically modulating the beam light when the rotary pacing current control is rotated; and detecting the beam of light after it is optically modulated to produce an electrical output that is representative of the rotation of the rotary pacing current control.

4. The method of claim 1, wherein the step of monitoring the operation of the manual input element comprises the step of monitoring the actuation of a pacemaker ON/OFF control.

5. The method of claim 1, wherein the step of monitoring the operation of the manual input element comprises the step of monitoring the operation of a function selection control.

6. The method of claim 1, wherein the step of monitoring the operation of the manual input element comprises the step of monitoring the actuation of a pacing START/STOP control.

7. The method of claim 1, wherein the step of monitoring the operation of the manual input element comprises the step of monitoring the operation of a mode selection control.

8. The method of claim 1, wherein the step of monitoring the operation of the manual input element comprises the step of monitoring the operation of a pacemaker ON/OFF control, a function selection control, a pacing START/STOP control, and a mode selection control.

9. The method of claim 1, further comprising the steps of;
   detecting the occurrence of a fault in the operation of the pacemaker; and
   establishing the pacing current as zero when the occurrence of a fault is detected.

10. A pacemaker, responsive to at least one manual input, for producing a controllable pacing current, said pacemaker comprising:
    current control means for rotationally producing an output indicative of the pacing current to be produced and for resetting that output to be indicative of a zero pacing current in response to the manual input; and
    controllable current source means, responsive to said output of said current control means, for producing the pacing current.

11. A pacemaker, responsive to at least one manual input, for producing a controllable pacing current, said pacemaker comprising:
    current control input means for rotationally producing an output indicative of the pacing current to be produced;
    processing means for responding to the operation of the manual input and for resetting the output of said input means to be indicative of a zero pacing current when the manual input is operation; and
    controllable current source means, responsive to said output of said current control means, for producing the pacing current.

12. The pacemaker of claim 11, wherein the current input means comprises:
    a rotatable knob;
    a shaft, coupled to said knob;
    a codewheel, coupled to said shaft and including a surface constructed to modulate light when the codewheel is rotated;
    light emission means for transmitting light to said codewheel, said codewheel modulating the light when rotated;
    light detection means for detecting the modulation of light by said codewheel to produce an electrical response; and
    conversion means for converting said electrical response into said output indicative of the pacing current to be produced.

13. The pacemaker of claim 12, wherein said knob, shaft, and codewheel are continuously and limitlessly rotatable.

14. A control circuit for allowing the current delivered by a pacemaker to be automatically controlled upon actuation of the pacemaker and for allowing an operator to control the current thereafter, said control circuit comprising:
    rotary pulse generation means for allowing the operator to produce an indication of a desired current; and
    processing means for setting the current to zero, upon actuation of the pacemaker and independent of the operation of said rotary pulse generation means, and for setting the current to the desired current thereafter, based upon the indication of the desired current produced by the rotary pulse generation means.

15. The control circuit of claim 14, wherein said rotary pulse generation means comprises:
    a rotatable knob;
    a shaft, coupled to said knob;
    light emission means for transmitting light to said codewheel, said codewheel modulating the light when rotated;
    light detection means for detecting the modulation of light by said codewheel to produce an electrical response; and
    conversion means for converting said electrical response into said output indicative of the pacing current to be produced.

* * * * *